US009295711B2

(12) United States Patent
Bernard et al.

(10) Patent No.: US 9,295,711 B2
(45) Date of Patent: Mar. 29, 2016

(54) COSMETIC AND THERAPEUTIC USE OF PROTEINS OF DJ-1 TYPE FOR TREATING SKIN DRYNESS

(75) Inventors: Dominique Bernard, Paris (FR); Lucie Simonetti, Vincennes (FR); Isabelle Castiel, Nice (FR)

(73) Assignee: L'OREAL, Paris (FR)

( * ) Notice: Subject to any disclaimer, the term of this patent is extended or adjusted under 35 U.S.C. 154(b) by 822 days.

(21) Appl. No.: 13/130,710

(22) PCT Filed: Nov. 19, 2009

(86) PCT No.: PCT/IB2009/055181
§ 371 (c)(1),
(2), (4) Date: Nov. 15, 2011

(87) PCT Pub. No.: WO2010/058364
PCT Pub. Date: May 27, 2010

(65) Prior Publication Data
US 2012/0114628 A1    May 10, 2012

Related U.S. Application Data

(60) Provisional application No. 61/193,486, filed on Dec. 3, 2008.

(30) Foreign Application Priority Data

Nov. 21, 2008   (FR) ..................................... 08 57916

(51) Int. Cl.
*A61K 38/00*   (2006.01)
*A61K 38/17*   (2006.01)
*A61K 8/64*   (2006.01)
*A61Q 19/00*   (2006.01)

(52) U.S. Cl.
CPC ............... *A61K 38/1709* (2013.01); *A61K 8/64* (2013.01); *A61Q 19/007* (2013.01)

(58) Field of Classification Search
None
See application file for complete search history.

(56) References Cited

U.S. PATENT DOCUMENTS

| 7,211,648 | B2 * | 5/2007 | Ghosh ........................... 530/350 |
| 2003/0119079 | A1 | 6/2003 | Hanash et al. |
| 2006/0153807 | A1 * | 7/2006 | Abeliovich et al. .......... 424/93.2 |

FOREIGN PATENT DOCUMENTS

WO          03 024302         3/2003

OTHER PUBLICATIONS

Oct. 2012 by Karen McKoy, MD, MPH, MERCK.*
Ghalbzouri EL. A. et al., "Fibroblasts Facilitate re-Epithelialization in Wounded Human Skin Equivalents", Laboratory Investigation, vol. 84, No. 1, pp. 102-112, ISSN: 0023-6837-1530-0307, XP002547901, (2004).
Nagakubo, D. et al., "DJ-1, A Novel Oncogene Which Transforms Mouse NIH3T3 Cells in Cooperation with Ras", Biochemical and Biophysical Research Communications, vol. 231, No. 2, pp. 509-513, ISSN: 0006-291X, XP002547902, (Feb. 13, 1997).
Tao, X. et al., "Crystal Structure of Human DJ-1, A Protein Associated with Early Onset Parkinson's Disease", The Journal of Biological Chemistry, vol. 278, No. 33, pp. 31372-31379, ISSN: 0021-9258, XP002547903, (Aug. 15, 2003).
Mehul, B. et al., "Identification and Cloning of a New Calmodulin-Like Protein from Human Epidermis", The Journal of Biological Chemistry, vol. 275, No. 17, pp. 12841-12847, (Apr. 28, 2000).
International Search Report issued Feb. 23, 2010 in PCT/IB09/055181 filed Nov. 19, 2009.

\* cited by examiner

*Primary Examiner* — Karlheinz R Skowronek
*Assistant Examiner* — Li Lee
(74) *Attorney, Agent, or Firm* — Oblon, McClelland, Maier & Neustadt, L.L.P.

(57) ABSTRACT

The present invention relates to the use, especially the cosmetic and/or therapeutic use, of the protein DJ-1, of polypeptides derived from this protein or of analogs thereof, of a nucleic acid sequence coding for such a polypeptide or of a modulator of the activity, stability or expression of such a polypeptide, especially for preventing and/or treating the signs of skin dryness. The invention also relates to the use of the protein DJ-1, of polypeptides derived from this protein or of analogs thereof or of a nucleic acid sequence coding for such a polypeptide, as a marker for evaluating the state of dryness of an epithelium.

2 Claims, No Drawings

SEQUENCE LISTING

<160> NUMBER OF SEQ ID NOS: 14

<210> SEQ ID NO 1
<211> LENGTH: 570
<212> TYPE: DNA
<213> ORGANISM: Homo sapiens

<400> SEQUENCE: 1

| | | | | | | |
|---|---|---|---|---|---|---|
| atggcttcca | aaagagctct | ggtcatcctg | gctaaggag | cagaggaaat | ggagacggtc | 60 |
| atccctgtag | atgtcatgag | gcgagctggg | attaaggtca | ccgttgcagg | cctggctgga | 120 |
| aaagacccag | tacagtgtag | ccgtgatgtg | gtcatttgtc | ctgatgccag | ccttgaagat | 180 |
| gcaaaaaaag | agggaccata | tgatgtggtg | gttctaccag | gaggtaatct | gggcgcacag | 240 |
| aatttatctg | agtctgctgc | tgtgaaggag | atactgaagg | agcaggaaaa | ccggaagggc | 300 |
| ctgatagccg | ccatctgtgc | aggtcctact | gctctgttgg | ctcatgaaat | aggctgtgga | 360 |
| agtaaagtta | caacacaccc | tcttgctaaa | gacaaaatga | tgaatggagg | tcattacacc | 420 |
| tactctgaga | atcgtgtgga | aaaagacggc | ctgattctta | caagccgggg | gcctgggacc | 480 |
| agcttcgagt | ttgcgcttgc | aattgttgaa | gccctgaatg | gcaaggaggt | ggcggctcaa | 540 |
| gtgaaggctc | cacttgttct | taaagactag | | | | 570 |

<210> SEQ ID NO 2
<211> LENGTH: 189
<212> TYPE: PRT
<213> ORGANISM: Homo sapiens

<400> SEQUENCE: 2

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
            180                 185

<210> SEQ ID NO 3
<211> LENGTH: 7
<212> TYPE: PRT
<213> ORGANISM: Homo sapiens

```
<400> SEQUENCE: 3

Ala Leu Val Ile Leu Ala Lys
1               5

<210> SEQ ID NO 4
<211> LENGTH: 8
<212> TYPE: PRT
<213> ORGANISM: Homo sapiens

<400> SEQUENCE: 4

Asp Gly Leu Ile Leu Thr Ser Arg
1               5

<210> SEQ ID NO 5
<211> LENGTH: 7
<212> TYPE: PRT
<213> ORGANISM: Homo sapiens

<400> SEQUENCE: 5

Asp Pro Val Gln Cys Ser Arg
1               5

<210> SEQ ID NO 6
<211> LENGTH: 14
<212> TYPE: PRT
<213> ORGANISM: Homo sapiens

<400> SEQUENCE: 6

Asp Val Val Ile Cys Pro Asp Ala Ser Leu Glu Asp Ala Lys
1               5                   10

<210> SEQ ID NO 7
<211> LENGTH: 15
<212> TYPE: PRT
<213> ORGANISM: Homo sapiens

<400> SEQUENCE: 7

Gly Ala Glu Glu Met Glu Thr Val Ile Pro Val Asp Val Met Arg
1               5                   10                  15

<210> SEQ ID NO 8
<211> LENGTH: 23
<212> TYPE: PRT
<213> ORGANISM: Homo sapiens

<400> SEQUENCE: 8

Gly Leu Ile Ala Ala Ile Cys Ala Gly Pro Thr Ala Leu Leu Ala His
1               5                   10                  15

Glu Ile Gly Phe Gly Ser Lys
            20

<210> SEQ ID NO 9
<211> LENGTH: 19
<212> TYPE: PRT
<213> ORGANISM: Homo sapiens

<400> SEQUENCE: 9

Gly Pro Gly Thr Ser Phe Glu Phe Ala Leu Ala Ile Val Glu Ala Leu
1               5                   10                  15

Asn Gly Lys

<210> SEQ ID NO 10
```

```
<211> LENGTH: 26
<212> TYPE: PRT
<213> ORGANISM: Homo sapiens

<400> SEQUENCE: 10

Gly Pro Gly Thr Ser Phe Glu Phe Ala Leu Ala Ile Val Glu Ala Leu
1               5                   10                  15

Asn Gly Lys Glu Val Val Ala Gln Val Lys
            20                  25

<210> SEQ ID NO 11
<211> LENGTH: 24
<212> TYPE: PRT
<213> ORGANISM: Homo sapiens

<400> SEQUENCE: 11

Lys Gly Leu Ile Ala Ala Ile Cys Ala Gly Pro Thr Ala Leu Leu Ala
1               5                   10                  15

His Glu Ile Gly Phe Gly Ser Lys
            20

<210> SEQ ID NO 12
<211> LENGTH: 8
<212> TYPE: PRT
<213> ORGANISM: Homo sapiens

<400> SEQUENCE: 12

Val Thr Thr His Pro Leu Ala Lys
1               5

<210> SEQ ID NO 13
<211> LENGTH: 9
<212> TYPE: PRT
<213> ORGANISM: Homo sapiens

<400> SEQUENCE: 13

Val Thr Val Ala Gly Leu Ala Gly Lys
1               5

<210> SEQ ID NO 14
<211> LENGTH: 16
<212> TYPE: PRT
<213> ORGANISM: Homo sapiens

<400> SEQUENCE: 14

Val Thr Val Ala Gly Leu Ala Gly Lys Asp Pro Val Gln Cys Ser Arg
1               5                   10                  15
```

COSMETIC AND THERAPEUTIC USE OF PROTEINS OF DJ-1 TYPE FOR TREATING SKIN DRYNESS

The present invention relates to the use, especially the cosmetic and/or therapeutic use, of the protein DJ-1, of polypeptides derived from this protein, for example obtained from its proteolysis, or of analogues thereof, of a nucleic acid sequence coding for such a polypeptide or of a modulator of the activity, stability or expression of such a polypeptide, for preventing and/or treating the signs of skin dryness and/or skin disorders associated with a state of skin dryness.

The invention also relates to the use of the protein DJ-1, of polypeptides derived from this protein or of analogues thereof, or of a nucleic acid sequence coding for such a polypeptide, as a marker for evaluating the state of dryness of an epithelium, and especially of the epidermis.

The epidermis is an epithelium, conventionally divided into a basal layer of keratinocytes especially containing cutaneous stem cells and constituting the germinative layer of the epidermis, a "spiny" layer formed from several layers of polyhedral cells arranged on the basal layer, a "granular" layer comprising one to three layers of "flattened cells" containing distinct cytoplasmic inclusions, keratohyalin grains, and finally an assembly of upper layers, known as the horny layer (or stratum corneum) and formed from keratinocytes at the final stage of their differentiation, known as corneocytes.

As a result of its sturdiness and its compact stratified structure, the stratum corneum provides a barrier function: it especially opposes transcutaneous water loss, also known as "transepidermal water loss".

Thus, one of the functions of the stratum corneum is to take up and retain the water contained in the epidermis, and any impairment of its structure and/or function may be reflected by changes in the hydration of the skin.

The skin is hydrated by means of the water from the deep layers and by sweat.

An imbalance in skin hydration may be reflected by profound consequences, both physiological and cosmetic.

Skin hydration disorders, and especially skin dryness, are often observed with age. However, such states may also be manifested in the case of young individuals.

The dry skin state may be of acquired or non-pathological constitutional origin or it may have a pathological constitutional origin.

Many external factors may lead to skin dryness or aggravate this state. Among these factors, mention may be made of climatic conditions such as cold or wind, sunlight, and exposure to certain chemical or therapeutic agents.

From a physiological viewpoint, dry skin is often associated with a lowering of the degree of hydration of the skin and also with a modification of the process of maturation of the stratum corneum, the most visible sign of which is the appearance of squamae on the surface of the skin.

From a sensory viewpoint, dry skin may be characterized by a sensation of skin tautness and/or tension.

Various methods exist for evaluating dry skin.

A first type of evaluation, performed from a strictly visual point of view, is based on a photographic atlas and uses a scale from 0 to 4 to note the score. The value 0 corresponds to an entirely normal skin, whereas the value 4 corresponds to a very dry skin. This method, which is subjective in nature, has the drawback of requiring the presence of visible cutaneous symptoms.

A second type of evaluation is based on biophysical measurements.

These methods are for the most part based on the electrical properties of skin, i.e. the capacitance, the conductance and the impedance of the skin. This is the case, for example, for measuring the hydration index of the horny layer by corneometry, based on the ability of skin to conduct an electrical current. This may be performed using various marketed machines, such as the corneometer from the company Courage & Khazaka.

Finally, other types of evaluation, occasionally termed "morphometric" techniques, relate to the analysis of the cutaneous microrelief or of the state of the cells at the skin surface, such as the evaluation of the "desquamation" by taking samples via "stripping" using adhesive of "D'squam" type from the company Cu-Derm.

These methods have the drawback of needing to be combined together in order to give a reliable measurement of the state of dryness of the skin.

Moreover, they also have the drawback of not giving any indications regarding the origin of the dry skin and thus the means for correcting it.

Consequently, there is a need for a new marker, especially a biological marker, that is capable of giving a reliable measurement of the state of an epithelium, and especially a state of dryness.

There is also a need for new tools for promoting the integrity and maturation of the stratum corneum and also for evaluating its state.

There is also a need for new tools and/or new cosmetic and/or dermatological targets that can be used for the purposes of preventing and/or relieving the physiological and/or sensory signs associated with dryness of an epithelium, and especially of an epidermis.

There is also a need for new cosmetic or dermatological targets for treating the state of dryness of an epithelium and especially of an epidermis.

There is also a need for new tools, especially new molecules, for treating and/or preventing a state of dryness of an epithelium, and especially of the epidermis.

The object of the present invention is to satisfy these needs.

The present invention results more particularly from the characterization by the inventors of an increase in the level of expression of the protein DJ-1 in the stratum corneum of a dry human epidermis, in comparison with the level of expression of this protein in a stratum corneum of normal epidermis. More particularly, the invention flows from the observation of an increased expression of the protein DJ-1 in aged and dry human epidermis, compared with a young or aged epidermis showing normal hydration.

The protein DJ-1 (or PARK 7) is a protein of 189 amino acids whose molecular weight is about 20 kDa. It appears that it exerts its functions in the form of a homodimer.

It is involved in many processes, such as cell proliferation, binding to RNA, male fertility, or the response to oxidative stress.

From a pathological viewpoint, the protein DJ-1 is known to be involved mainly in two types of pathology, namely certain cancers and neurodegenerative diseases, such as Parkinson's disease.

Specifically, as an oncogenic, the protein DJ-1 has been observed as being deregulated in breast and prostate cancers. It has also been shown that it may collaborate with another cellular oncogene, the Ras oncogene.

Moreover, various studies suggest the involvement of the protein DJ-1 in an autosomal recessive form of Parkinson's disease, known as "Parkinson Disease 7".

It has especially been shown that various persons suffering from this disease have an identical mutation in the gene coding for DJ-1, the consequence of which is loss of function of the protein DJ-1. Since Parkinson's disease is manifested by the gradual death of the dopaminergic neurons, this study thus suggests that the protein DJ-1 is involved in the survival of these neurons. It is on account of this role in Parkinson's disease that the protein DJ-1 is also often referred to by the name PARK 7.

To the inventors' knowledge, the protein DJ-1 has never been identified hitherto as being a protein whose expression varies as a function of the skin typology, i.e. an increased level of expression in dry human stratum corneum relative to that present in normal human stratum corneum.

Thus, contrary to all expectation, the protein DJ-1 also proves to be a potential marker of the physiological state of the skin, especially in terms of dryness. Specifically, as emerges from the tests featured hereinbelow, the inventors have found, unexpectedly, firstly an expression of this protein in the stratum corneum, and secondly a significant increase in its expression in stratum corneum sampled from a dry skin, in comparison with stratum corneum sampled from a normal skin.

Consequently, according to one of its first aspects, a subject of the present invention is a cosmetic or non-therapeutic use of an effective amount of at least one polypeptide derived from the protein DJ-1, and especially of an amino acid sequence coded for by a nucleic acid sequence wholly or partially represented by the sequence represented by SEQ ID No. 1, an analogue thereof or a fragment thereof, of at least one nucleic acid sequence coding for such a polypeptide or of at least one modulator of the activity, stability or expression of such a polypeptide, as an agent that is useful for preventing and/or treating the signs of skin dryness, in particular for preventing and/or treating dehydration of an epidermis.

According to another of its aspects, a subject of the present invention is also the use of an effective amount of at least one polypeptide derived from the protein DJ-1, and especially of an amino acid sequence coded for by a nucleic acid sequence wholly or partially represented by a sequence represented by SEQ ID No. 1, an analogue thereof or a fragment thereof, of at least one nucleic acid sequence coding for such a polypeptide or of at least one modulator of the activity, stability or expression of such a polypeptide, for the preparation of a composition, especially a therapeutic composition, for preventing and/or treating the signs of skin dryness, in particular for preventing and/or treating dehydration of an epidermis.

The term "signs of skin dryness" means not only all the modifications of the outer appearance of the skin due especially to the dehydration of the epidermis, such as the rough and flaky appearance, as well as the decreased suppleness, but also the sensations associated with the phenomenon of dryness, such as itching and/or tautness. It may, in fact, occur that these sensations are felt by a person without any visual symptom being necessarily perceptible.

According to one embodiment of the invention, a use in accordance with the invention may be more particularly intended for preventing and/or treating the signs of non-pathological constitutional or acquired skin dryness.

For the purposes of the present invention, the term "effective amount" is intended to denote the minimum amount required for observation of the expected effect, i.e. a cosmetic effect or a therapeutic effect, it being understood that the effective amounts required for obtaining a cosmetic effect or a therapeutic effect may be, where appropriate, identical or different.

For the purposes of the invention, the term "cosmetic use" is intended to denote a use intended mainly for affording an aesthetic effect and/or comfort.

For the purposes of the invention, the term "therapeutic composition" is intended to denote a composition intended for affording a prophylactic or curative effect with regard to epithelial and especially epidermal disorders, recognized as reflecting a pathological state.

For the purposes of the invention, the terms "prophylactic" and "preventive" mean a reduction of the risk of occurrence of a phenomenon, for example a pathology.

A composition in accordance with the invention may, in particular, be intended for preventing and/or treating dryness of an epidermis, and especially a defect of hydration of the stratum corneum.

A composition in accordance with the invention may in particular be intended for preventing and/or treating itching and/or tautness sensations in a dry epithelium.

According to yet another of its aspects, the present invention also relates to the use of at least one polypeptide in accordance with the invention, or of at least one nucleic acid sequence coding for the said polypeptide, as a tool for the in vitro or ex vivo characterization of the state of an epithelium, and especially of an epidermis, the said state in particular being a state of dryness.

More specifically, according to another of its aspects, the present invention relates to a process, especially a cosmetic, non-invasive process, for characterizing the state of dryness of an epithelium, especially of an epidermis, comprising at least the qualitative or quantitative characterization of the expression and/or biological activity of a polypeptide in accordance with the invention, i.e. the protein DJ-1 or a derivative or fragment thereof.

According to another embodiment variant, the datum or value obtained may be assessed in comparison with a reference datum or value, obtained, for example, from at least one epithelium, especially an epidermis, different from that undergoing the characterization, and whose state is known. By way of example of reference epidermis, it may be either an epidermis of a second individual who has normal skin and distinct from a first individual on whom the characterization is performed, or a region of the epidermis of the same individual on whom the characterization is performed, but chosen from an area of skin that shows physiological hydration.

According to another of its aspects, the present invention is also directed towards a process, especially a cosmetic, non-invasive process, for characterizing the efficacy of a cosmetic or therapeutic treatment aimed at compensating for the signs of skin dryness, comprising at least the qualitative or quantitative characterization of the expression and/or biological activity of a polypeptide in accordance with the invention, i.e. of the protein DJ-1 or a derivative or fragment thereof.

According to one embodiment variant, the datum obtained after the characterization may also be examined in comparison with a reference value or datum. This reference value or datum may be a datum obtained from the epithelium, especially from the epidermis, to be subjected to the treatment, prior to the administration of the said treatment or in a shorter chronological delay with regard to the treatment start date.

As emerges from the description that follows, the processes according to the invention are particularly advantageous insofar as their implementation does not require an invasive operation.

The processes of the invention may be performed in vitro, ex vivo or in vivo.

Specifically, the localization by the inventors of the novel dryness biomarker, namely the protein DJ-1, in the stratum corneum permits a quantitative or qualitative characterization of the expression of this protein by simple topical sampling. The sampling method may be, for example, a technique of "stripping" type that consists in applying to the epithelium under consideration, such as an epidermis, a portion of adhesive tape. On detaching this adhesive tape, a fraction of the epithelium, for example an epidermal fraction, is removed. After protein extraction, it is analysed via conventional methods, such as immunoenzymatic assay or, more particularly, a western blot analysis.

Dry Skin

A dry skin has a rough feel, appears covered with squamae and is essentially manifested by a sensation of tautness and/or tension.

Dry skin is in fact accompanied by a desquamation disorder and presents different stages as a function of the severity of this desquamation. When the skin is slightly dry, these squamae are abundant but sparingly visible to the naked eye, and removal takes place corneocyte by corneocyte. They are increasingly infrequent but increasingly visible to the naked eye when this disorder worsens, and the patches may comprise several hundred corneocytes, thus representing more or less large patches, known as squamae.

The origin of this skin dryness may be of constitutional or acquired type.

In the case of constitutional dry skin, two categories may be distinguished: pathological skin and non-pathological skin.

Pathological constitutional dry skin is essentially represented by atopic dermatitis and ichthyosis. It is virtually independent of the external conditions, and arises from known or unknown genetic modifications. Among the known genetic modifications that affect cutaneous hydration, examples that may be mentioned include modifications of the Transglutaminase 1 gene or those of the Filaggrin gene.

In the case of non-pathological constitutional dry skin, the severity of the state of dryness may, for its part, depend on external factors. Senile skin (characterized by a general decrease in cutaneous metabolism with age), fragile skin (very sensitive to external factors and often accompanied by erythema and rosacea) and xerosis vulgaris (of probable genetic origin and mainly manifested on the face, the limbs and the back of the hands) are included in this skin category.

In the case of acquired dry skin, the intervention of external parameters such as exposure to chemical agents, harsh climatic conditions, sunlight or certain therapeutic treatments (for example retinoids) is a determining factor. Under these external influences, the epidermis may then become momentarily and locally dry. This may concern any type of epidermis.

Irrespective of its origin, a skin suffering from skin dryness generally presents the following signs, namely a rough and flaky feel, and also decreased suppleness and elasticity.

Dry skin, also known as "xerosis", may appear at any age and may be unconnected to a pathological condition. It will be referred to in this case as "acquired" dryness.

However, xerosis becomes more frequent and debilitating with age, especially in women. This is known as senile xerosis. Moreover, women generally suffer a worsening of skin dryness during the menopause, probably due to the hormonal deregulation characteristic of this phenomenon. The areas most affected are the lower legs, the back of the forearms and the hands.

As mentioned previously, acquired dryness may be subject to the influence of external factors. For example, the appearance of dry skin may be promoted by cold, dry, wintry weather. This is known as winter xerosis. The skin dryness may also be induced by an exogenous stress, of chemical origin, for example of anionic detergent type, or alternatively of mechanical origin (chafing or shaving).

According to one embodiment, a dry skin under consideration in the invention may in particular be a young skin.

Moreover, although no study has demonstrated an incidence of dryness on the origin and formation of wrinkles and fine lines, which are essentially attributable to ageing, in visual terms a dry skin makes wrinkles and fine lines more apparent.

According to another aspect, the invention relates to aged and dry skin.

Moreover, from a sensory viewpoint, skin dryness is characterized by a sensation of tautness and/or itching. For obvious reasons, these manifestations are not only sources of discomfort, or even of pain, but also unaesthetic.

Thus, there is a need for novel active agents capable of exerting a beneficial action in the treatment of skin dryness, not only from a therapeutic viewpoint, but also from an aesthetic viewpoint.

Polypeptide

According to one embodiment, a polypeptide that is suitable in the invention may have an amino acid sequence wholly or partially represented by a sequence represented by SEQ ID No. 2, an analogue thereof, or a fragment thereof.

For the purposes of the present invention, unless otherwise indicated, the term "protein DJ-1" is generally intended to denote the sequence (SEQ ID No. 2) of the protein, which may or may not have undergone post-translational modifications.

Among these post-translational modifications, mention may be made in particular of sumoylation of the lysine residue in position 130 of the protein.

It is moreover known that the primary sequence of a polypeptide, i.e. the amino acid sequence, determines sites specifically recognized by enzymes of protease type, such as trypsin, which, once these sites have been recognized, will induce the cleavage of the polypeptide by proteolysis. This proteolysis results in the generation of various peptides, or proteolysis fragments, of the protein DJ-1.

The inventors have detected the presence of such peptides in the stratum corneum.

Consequently, the invention also covers the proteolysis fragments of the protein DJ-1.

Thus, according to one particular embodiment, a polypeptide that is suitable in the invention may have an amino acid sequence chosen from SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13 and SEQ ID No. 14.

The term "polypeptide analogue" is intended to denote any polypeptide that has sequence homology, in particular with respect to one of the characteristic sequences of the said polypeptide, and also biological activity of the same nature.

This compound may be a peptidomimetic agent.

The homology may be at least 85%, for example at least 90%, and for example at least 95%. The homology may be determined by visual comparison or by means of any software tool generally used in the field, such as the BLAST programs available at www.ncbi.nlm.nih.gov and used with the configured default parameters.

The sequence homology may result from modifications derived from mutation or variation in the sequences of the peptides according to the invention, originating either from the deletion or insertion of one or more amino acids, or from the substitution of one or more amino acids in the characteristic sequences of a polypeptide according to the invention.

For the purposes of the invention, the term "polypeptide fragment" is intended to denote any portion of a polypeptide in accordance with the invention comprising at least 4, at least 6, in particular at least 8 and more particularly at least 12 consecutive amino acids of the said polypeptide, and substantially similar biological activity.

The term "characteristic sequence of the polypeptide" is intended to denote, especially with regard to the protein DJ-1, the sequence represented by SEQ ID No. 2.

In general, the polypeptide analogues may comprise conservative substitutions relative to the amino acid sequence of the natural polypeptide.

Several of these modifications may be combined.

As examples of mutations that may be considered in the present invention, mention may be made, in a non-exhaustive manner, of the replacement of one or more amino acid residues with amino acid residues having a similar hydropathic index, without, however, substantially affecting the biological properties of the polypeptide, and especially its biological activity, such as its activity on stimulating the proliferation and/or migration and/or terminal differentiation of keratinocytes.

The hydropathic index is an index attributed to amino acids as a function of their hydrophobicity and their charge (Kyte et al. (1982), J. Mol. Biol., 157: 105).

A polypeptide or analogue also targeted by the present invention may be a polypeptide that has undergone one or more post-translational modification(s).

The term "post-translational modification(s)" is intended to cover all the modifications that a peptide or a protein is liable to undergo after its synthesis in a cell, for instance one or more phosphorylation(s), one or more thiolation(s), one or more acetylation(s), one or more glycosylation(s), one or more lipidation(s), such as a farnesylation or a palmitoylation, or a structural rearrangement of the type for formation of disulfide bridges and/or of cleavage type within the peptide sequence.

An analogue according to the invention moreover has substantially the same biological activity as the natural polypeptide.

According to one embodiment, a polypeptide that is suitable for use in the invention may also be a natural or synthetic polypeptide, which may be obtained, where appropriate, after enzymatic or chemical lysis of the protein DJ-1 or via chemical or biological synthesis or via extraction from a biological tissue, for instance the skin, naturally expressing this polypeptide or after transfection thereof, and also the various post-translational forms thereof, or any natural or synthetic polypeptide whose sequence totally or partially comprises (in whole or in part) an abovementioned amino acid sequence, for example the variants and analogues.

A person skilled in the art may obtain a polypeptide in accordance with the invention by means of recombinant DNA-based processes, for instance those described in the manual *Molecular Cloning—A Laboratory Manual* (2nd edition), Sambrook et al., 1989, Vol. I-III, Cold Spring Harbor Laboratory, Cold Spring Harbor, N.Y., (Sambrook).

According to another embodiment, a polypeptide that is suitable for use in the invention may also be a polypeptide as defined previously in which at least one residue has been replaced with an amino acid residue of similar hydropathic index, as defined previously.

According to another embodiment, a polypeptide that is suitable for use in the invention may also be a polypeptide as defined previously, fused with another polypeptide, a hydrophilic or hydrophobic targeting agent, a bioconversion precursor, or a luminescent, radioactive or colorimetric marker.

In a non-limiting manner, as examples of compounds that may be coupled with a polypeptide in accordance with the invention, mention may be made of fluorescent proteins such as "Green Fluorescent Protein", fluorescent chemical compounds such as rhodamine, fluorescein or Texas Red®, phosphorescent compounds, radioactive elements, such as $^3$H, $^{14}$C, $^{35}$S, $^{121}$I or $^{125}$I, or colorimetric markers, for instance chromogenic substrates that are sensitive to the action of galactosidase, peroxidase, chloramphenicol acetyltransferase, luciferase or alkaline phosphatase.

Depending on the nature of the compounds that may be coupled with a polypeptide in accordance with the invention, the coupling may be performed via chemical processes, especially using reactive chemical functions, or via molecular biology processes known to those skilled in the art.

Nucleic Acid Sequences

According to one embodiment, the present invention also relates to nucleic acid sequences coding for a polypeptide of the invention and to their implementation in the various uses and processes in accordance with the invention.

Thus, the present invention also relates to the use of nucleic acid sequences, especially deoxyribonucleic acid or ribonucleic acid sequences, coding for a polypeptide in accordance with the invention, especially the sequences corresponding to at least one nucleic acid sequence represented by SEQ ID No. 1, analogues thereof or a fragment thereof, for the preparation of a composition in accordance with the invention.

For the purposes of the present invention, the term "fragment of a nucleic acid sequence" means a nucleic acid sequence coding for all or part of a polypeptide in accordance with the invention, or an analogue thereof, and in particular a nucleic acid sequence represented by SEQ ID No. 1, or an analogue thereof.

The term "analogue of a nucleic acid sequence" is intended to denote any nucleic acid sequence, possibly resulting from degeneracy of the nucleic acid code, and coding for a polypeptide whose sequence is identical or analogous to that of the polypeptide coded for by the said nucleic acid sequence.

The nucleic acid sequences may be derived from any possible origin, i.e. either animal origin, in particular from mammals and even more particularly humans, or plant origin, or from microorganisms (viruses, phages and bacteria, inter alia) or from fungi, without prejudice as to whether or not they are naturally present in the said organism of origin.

In the present case, the invention also relates to the use of isolated and purified nucleic acid fragments coding for the polypeptides under consideration according to the invention.

A nucleic acid sequence in accordance with the invention may comprise a sense, antisense or interferent sequence corresponding to a sequence coding for a polypeptide in accordance with the invention.

Thus, the present invention also relates to the use of nucleic acid sequences, especially the deoxyribonucleic acid or ribonucleic acid sequences, coding for a polypeptide in accordance with the invention.

The nucleic acid sequences according to the invention may especially be used for preparing the corresponding sense or antisense ribonucleic acid sequences.

A subject of the invention is also the use of any polynucleotide, or ribonucleic or deoxyribonucleic acid sequence, comprising a sense or antisense sequence, especially "Small interferent RNA" (SiRNA) corresponding at least to the nucleic acid sequence SEQ ID No. 1, or an analogue thereof.

Modulator

According to another embodiment, the invention relates to the use of a modulator of the expression and/or stability and/or activity of a polypeptide in accordance with the invention.

For the purposes of the invention, the term "modulate", with regard to a given effect, means the action of stimulating or inhibiting this effect.

For the purposes of the present invention, the term "modulator or chemical or biological compound capable of modulating the biological activity and/or the expression" means any compound capable of acting, directly or indirectly, on at least one polypeptide in accordance with the invention, or a nucleic acid sequence coding therefor, or on an intracellular or extracellular signalling pathway element, or a metabolic pathway element, involving the said polypeptide, or on an element involved in regulating the transcription and/or translation of a nucleic acid sequence coding for the said polypeptide, and also in the regulation of its stability.

The term "biological activity" is especially intended to denote, with regard to the protein DJ-1, the biological activity of the protein represented by the sequence SEQ ID No. 2.

This modulator may be an activator or inhibitor of the expression of a polypeptide of the invention, or alternatively a regulator of the stability of the said polypeptide.

In particular, a modulator may be an inhibitor of the expression of a polypeptide of the invention.

As non-limiting illustrations, among the stability regulators, as agents that reduce the stability of a polypeptide, mention may be made especially of compounds that stimulate proteolytic degradation, such as proteases, ion-chelating agents, sulfonic derivatives, urea derivatives, reducing agents, α- or β-hydroxy acids, ascorbic acid and nicotinamide, and mixtures thereof.

According to one preferred embodiment, the modulator is an agent that reduces the stability of the polypeptides in accordance with the invention, by stimulating their proteolytic degradation.

It is understood that all the cosmetic or therapeutic compositions under consideration according to the invention use a physiologically acceptable medium.

For the purposes of the present invention, the term "physiologically acceptable medium" is intended to denote a medium that is suitable for the application of a composition to an epithelium or a keratin material, such as the skin, the scalp, the lips, mucous membranes and keratin fibres such as head hair, the nails and bodily hair, or, where appropriate, oral or parenteral application.

For the purposes of the present invention, the term "therapeutic" is intended to denote a composition that can be used in the context of a prophylactic and/or curative treatment, or of a method for evaluating the state of dryness of an epithelium, and especially of the epidermis.

According to another embodiment, a cosmetic or therapeutic composition in accordance with the invention may also comprise at least one cosmetic and/or therapeutic active agent.

As examples of active agents that may be used in the context of the present invention, mention may be made of cosmetic oils, such as silicone oils, plant oils of triglyceride type, hydrocarbon-based oils such as Parleam oil, and esters of fatty acids and of fatty alcohols.

It may also be possible to use other active agents that can improve the state of the skin, such as hydrating or moisturizing active agents, or active agents that can improve the natural lipid barrier, such as ceramides, cholesteryl sulfates and/or fatty acids, and mixtures thereof.

It may also be possible to use enzymes that have activity on the skin, such as proteases, lipases, glucosidases, amidases, cerebrosidases and/or melanases, and mixtures thereof.

Other examples of active agents that are suitable for use in the present invention include: analgesic active agents, anti-yeast active agents, antibacterial active agents, antiparasitic active agents, antifungal active agents, antiviral active agents, steroidal anti-inflammatory active agents, anaesthetic active agents, anti-pruriginous active agents, keratolytic active agents, free-radical-scavenging active agents, anti-seborrhoeic active agents, antidandruff active agents, antiacne active agents, active agents for preventing ageing of the skin and/or for improving its state, anti-dermatitis active agents, anti-irritant active agents, immunomodulating active agents, active agents for treating dry skin, antiperspirant active agents, anti-psoriatic active agents, anti-UV active agents, antihistamine active agents, cicatrizing active agents, self-tanning active agents, antioxidants such as green tea or active fractions thereof, glycerol, laponite, caffeine, aromatic essential oils, colorants, depigmenting active agents, liporegulators, softening, refreshing, deodorizing, desensitizing, bleaching or nourishing active agents, and active agents for reducing cutaneous differentiation and/or proliferation and/or pigmentation, and mixtures thereof.

In general, any composition of the invention may be applied to the skin (to any area of bodily skin) or to mucous membranes (oral, jugal, gingival, genital, conjunctival, etc.).

In a known manner, a cosmetic composition may also contain adjuvants that are common in cosmetics, such as hydrophilic or lipophilic gelling agents, hydrophilic or lipophilic additives, preserving agents, antioxidants, solvents, fragrances, fillers, screening agents, odour absorbers and dyestuffs.

The amounts of the various constituents of the compositions according to the invention are those conventionally used in the fields under consideration.

The amount of chemical or biological compound or of polypeptide, nucleic acid sequence or modulator in accordance with the invention contained in a composition according to the invention, also known as the "effective amount", depends, of course, on the nature of the compound and on the desired effect, and may thus vary within a wide range.

To give an order of magnitude, a composition may contain a modulator in accordance with the invention or a polypeptide in an amount representing from 0.00001% to 50% of the total weight of the composition, in particular in an amount representing from 0.001% to 10% of the total weight of the composition and more particularly in an amount representing from 0.1% to 1% of the total weight of the composition.

A composition according to the invention may be more particularly intended for reducing and/or treating a hydration defect, and especially dryness, which is liable to deteriorate the state of an epithelium, and especially of an epidermis.

According to another aspect, the present invention also relates to the use of at least one polypeptide in accordance with the invention or of at least one nucleic acid sequence coding for the said polypeptide, as a tool for the in vitro or ex vivo characterization of the state of an epithelium, and especially of an epidermis, the said state especially being a state of dryness.

Thus, according to another of its aspects, the present invention relates to non-invasive processes for characterizing the state of dryness of the surface of a non-pathological epidermis or alternatively the efficacy of a cosmetic or therapeutic treatment aimed at qualitatively or quantitatively characterizing the expression of the protein DJ-1 or a derivative or fragment thereof.

These processes are particularly advantageous insofar as their implementation does not necessarily require the use of an operating technique to perform such a characterization. An extract of the epidermis may thus be obtained by simple "stripping" and directly analysed via a conventional analysis technique especially as described previously.

According to one embodiment, a process for characterizing the state of dryness of an epithelium, for example an epidermis, comprises at least the steps consisting in:

a) determining, in a sample of the said epithelium, the content of a polypeptide in accordance with the invention, or of a nucleic acid sequence coding for the said polypeptide, and b) comparing the said content determined in step a) with a reference value.

Advantageously, a process of the invention is non-invasive.

A process of the invention is advantageously performed on an isolated sample.

According to one embodiment, a process according to the invention may be performed on a sample of epithelium, and especially of epidermis, taken from an individual.

A process according to the invention may also be performed on a sample of epithelium, and especially of epidermis, taken from an epithelial and especially an epidermal cellular model, or from a reconstructed isolated skin in order to qualify its state.

The taking of a sample of epithelium may be performed via any method known to those skilled in the art.

A process according to the invention may be performed in vivo, in vitro or ex vivo.

A reference value may be, for example, a content of polypeptide or of nucleic acid sequence determined on a sample of epidermis taken from an epithelium, and especially a normal skin, i.e. skin that is physiologically satisfactory, such as, for example, a hydrated skin.

The measurement of a reference value may be performed in parallel with or following the determination of the said content of a polypeptide or of a nucleic acid sequence.

Comparison of a determined content with a reference value may enable evaluation of a deviation relative to this value.

Analysis of the intensity and/or nature of this deviation (negative or positive) may be informative as regards the state of the epidermis.

The characterization of a state of dryness of an epidermis may be indicative of a possible cutaneous disorder that may be corrected by using compounds capable of modulating the expression of a polypeptide of the invention.

According to one embodiment, a process according to the invention may be performed in a process of in vivo, in vitro or ex vivo diagnosis of dryness of an epithelium, and especially of the epidermis, in an individual.

A polypeptide that is suitable for use in a process according to the invention may advantageously be the protein DJ-1.

The determination of a content of polypeptide in accordance with the invention or of nucleic acids in accordance with the invention in a sample of epidermis may be performed via any protocol known to those skilled in the art.

The expression of a nucleic acid sequence may be determined, for example by means of oligonucleotide probes, via any protocol known to those skilled in the art.

As examples of methods for detecting nucleic acid sequences, mention may be made of the polymerase-chain reaction, in quantitative mode (Q-PCR) or non-quantitative mode (PCR), in the presence or absence of reverse transcriptase (RT-PCR or Q-RT-PCR), Northern blotting, the "ribonuclease protection assay" method, methods with DNA chips, methods with transcriptome chips, methods with oligonucleotide chips, and in situ hybridization methods.

As examples of agents that are suitable for detecting a nucleic acid sequence, and in particular an mRNA sequence, mention may be made of labelled nucleic acid probes that can hybridize to the said sequence.

Such a nucleic acid probe may be readily obtained via any method known to those skilled in the art.

Thus, the nucleic acid sequences in accordance with the invention may be used for preparing sense and/or antisense oligonucleotide primers, which hybridize under conditions of high stringency to the sequence SEQ ID No. 1 or an analogue thereof.

The expression of a nucleic acid sequence in accordance with the invention may be compared with a reference value obtained, for example, by performing a process in accordance with the invention in the absence of test compound.

The expression of a nucleic acid sequence may also be determined, indirectly, by determining the expression of the polypeptide coded for by the said sequence, by means of any technique known in the field, such as Western blotting, ELISA, the Bradford or Lowry method, or as indicated hereinbelow.

A nucleic acid sequence that is suitable for use in a process according to the invention may advantageously be a nucleic acid sequence coding for the protein DJ-1, for example of mRNA type.

The determination of the content of a polypeptide in accordance with the invention may be performed via any method known to those skilled in the art.

Examples of polypeptide detection methods that may be mentioned include Western blotting, slot-blotting, dot-blotting, ELISA (Enzyme-Linked ImmunoSorbent Assay) methods of singleplex or multiplex type, proteomic and glycomic methods, staining of polypeptides in a polyacrylamide gel with a silver-based stain, with Coomassie blue or with Sypro, immunofluorescence, UV absorption, immunohistochemical methods with standard, electron or confocal microscopy, FRET (fluorescence resonance energy transfer), TR-fret (time-resolved FRET) methods, FLIM (fluorescence lifetime imaging microscopy) methods, FSPIM (fluorescence spectral imaging microscopy) methods, FRAP (fluorescence recovery after photobleaching) methods, reporter-gene methods, AFM (atomic force microscopy) methods, surface plasmonic resonance methods, microcalorimetry methods, flow cytometry methods, biosensor methods, radioimmunoassay (RIA) methods, isoelectric focalization methods, and enzymatic tests, methods using peptide chips, sugar chips, antibody chips, mass spectrometry methods, and spectrometry methods of SELDI-TOF type (Ciphergen).

The processes in accordance with the invention may be performed on a sample, for example an isolated sample, of epithelium, especially of epidermis, obtained from a skin biopsy or from an epithelial cellular model, for example an epidermal cellular model, or more advantageously from a non-invasive surface sampling, especially by adhesive "tape stripping" of stratum corneum or by simple washing.

A sample of epidermis may be collected via any method known to those skilled in the art.

These methods may be performed via techniques known as "stripping".

These strippings are performed using adhesive surfaces applied to the surface of the epidermis, for instance Blenderm® from 3M, D'squam (commercial adhesive from Cu-Derm), cyanoacrylate adhesive or the varnish "stripping" method. By means of these "strippings", the adherent corneocytes and the contents of their intercellular spaces can be sampled and subsequently subjected to extraction in order to access the protein content.

The collecting of a sample suitable for use in the process may also be performed more directly by "washing" the skin surface, for example using accessories of blade turbine type, of coil cell type (as described in patent FR 2 667 778) associated with a fluid circuit, or simply by adding/collecting a drop of buffer at the surface of the skin.

As a guide, other sampling methods suitable for use in the invention may be mentioned, such as methods involving scraping the upper part of the stratum corneum using a twin-blade system. This technique makes it possible to collect squamae, which can then be directly analysed via various techniques to determine the mineral, amino acid or fat contents.

Additionally, it may be envisaged to detect the presence of a polypeptide in accordance with the invention by means of an antibody, where appropriate in a labelled form.

An antibody that may be used as a tool for evaluating the state of an epidermis may be obtained via any process known to those skilled in the art, as described in "*Antibodies: A Laboratory Manual*", Cold Spring Harbor Laboratory Press, Cold Spring Harbor, N.Y. (1990). Advantageously, the antibodies used may be recombinant antibodies, such as those developed by the company Antibodies-by-design.

The present invention also relates to a non-therapeutic process for demonstrating an effect of a treatment capable of causing regression of the signs of dryness of an epithelium, especially itching and/or tautness sensations, in an individual, comprising at least the steps consisting in:

a) performing, before the treatment, at least a first determination, in a first sample of an epithelium taken from the said individual, of a biological activity and/or of the expression of a polypeptide in accordance with the invention, or of the expression of a nucleic acid sequence coding for the said polypeptide, b) performing, after the treatment, at least a second determination, in a second sample of an epithelium taken from the said individual, of the said biological activity and/or of the said expression of the said polypeptide or of the said expression of the said nucleic acid sequence determined in step a), and c) comparing the first and second determinations, especially in order to deduce therefrom information relating to at least one effect of the treatment.

Such a treatment may in particular be a cosmetic treatment.

In particular, the treatment whose effect it is intended to evaluate may be a treatment intended to relieve or reduce the signs of skin dryness.

The biological activity of a polypeptide may be determined via any method known to those skilled in the art. For example, and in a non-limiting manner, mention may be made of cell culture methods followed by a characterization of differentiation markers, for instance keratin 10 or filaggrin, or proliferation markers, for instance KI 67 and PCNA.

Advantageously, a polypeptide used in a process according to the present invention may be the protein DJ-1.

The expression of a polypeptide may be determined as indicated previously.

According to another aspect, the present invention relates to a cosmetic process for treating the signs of skin dryness, comprising at least one step that consists in applying to at least part of the skin, mucous membranes and/or keratin fibres at least one cosmetic composition in accordance with the invention.

For the purposes of the present invention, the term "one" should be understood, unless otherwise mentioned, as meaning "at least one".

The examples featured below are given as non-limiting illustrations of the invention.

EXAMPLE I

Analysis of the Expression of the Protein DJ-1 in a Dry Stratum Corneum Versus a Normally Hydrated Stratum Corneum The analyses are performed using samples collected by varnish "stripping" performed on the legs of various individuals.

The individuals included in the study are divided into four groups:

the DA group corresponds to group 1: dry menopausal n=15, the NA group corresponds to group 2: normal menopausal n=13, the DY group corresponds to group 3: dry young n=16, the NY group corresponds to group 4: normal young n=14.

Selection of the individuals from the "dry skin" groups (DA and DY) is performed by an expert, on the basis of a visual evaluation, by comparison with a photographic atlas, of the state of skin dryness of each individual on the legs.

1: Preparation of Acetone Powders

Two varnish "strippings" (B. Mehul et al., J. Biol. Chem., 2000, Apr. 28; 275(17): 12841-7) of 10 $cm^2$ are placed in 20 ml of acetone. The corneocytes become detached. The mixture is filtered through a 40 µm Nylon membrane. Three successive rinses are performed with the same volume of acetone. The suspension is finally filtered on a vacuum pump. The acetone powders of stratum corneum in dry form are obtained.

2: Extraction of the Samples

An extraction is performed under denaturing conditions. To do this, a prewash is performed with a volume (100 µl) of PBS buffer (phosphate-buffered saline)+0.1% Triton X100 which is added per mg of acetone powder. The mixture is ground in a Potter mill and centrifuged. The corneocyte pellet is collected. It is extracted with the same volume (100 µl/mg) of Laemmli buffer 0.0625 mM Tris pH 6.8, 200 mM DTT, 2% SDS, 10% glycerol. The mixture is boiled for 10 minutes and then ground and centrifuged for 10 minutes at 10 000×g. The supernatant is collected. A protein assay is performed according to the Bradford technique with the Bradford reagent (Bio-Rad Protein Assay). The samples are adjusted to 1 mg/ml.

3: Analysis of the Proteins by Western Blotting

The proteins are separated by SDS-PAGE electrophoresis. After semi-dry transfer onto a PVDF membrane (Immobilon-P Millipore) according to a standard protocol, the proteins are incubated with the anti-DJ-1 primary antibody (Abcam, ab 4150) overnight at 4° C. The second incubation is then performed with the secondary antibody (goat anti-mouse IgG-HRP conjugate; Bio-Rad) directed against the primary antibody, for 1 hour 30 minutes at room temperature. The presence of the protein DJ-1 on the membrane is revealed by immunodetection using the ECL plus kit (Amersham). The membrane is then stained with Amidoblack to detect the total proteins present on the membrane. The image is acquired using a Fluor S Max machine (Bio-Rad) and the bands are quantified using the Quantity-one software (Bio-Rad).

4: Results

The results are expressed in delta cnt*mm$^2$ of the protein of interest/delta cnt*mm$^2$ of the total proteins.

Methodology:

−2-factor analysis of variance, Age and Type of skin, taking into account the interaction of these two factors +1-factor analysis of variance (group) and Tukey multiple comparison test. As the normality and homoscedasticity conditions were not verified, the analysis was performed after logarithmic transformation.

The statistical analysis was performed with the SAS version 8.2 and SPSS version 12 software packages.

All the tests were performed at the 5% bilateral threshold.

The table below collates the mean results and their standard error of mean (SEM).

| Group | DJ-1 | SEM DJ-1 |
|---|---|---|
| DA | 4189 | 518 |
| NA | 4485 | 658 |
| DY | 4521 | 558 |
| NY | 3644 | 352 |

A significant variation in expression of the protein DJ-1 according to the skin typology is noted: specifically, its expression is significantly increased in the "dry skin" groups (DY and DA), compared with the "normal skin" groups (NY and NA) ($p=0.008$).

```
                       Sequence listing

SEQ ID NO 1
atggcttcca aaagagctct ggtcatcctg gctaaaggag cagaggaaat ggagacggtc
atccctgtag atgtcatgag gcgagctggg attaaggtca ccgttgcagg cctggctgga
aaagacccag tacagtgtag ccgtgatgtg gtcatttgtc ctgatgccag ccttgaagat
gcaaaaaaag agggaccata tgatgtggtg gttctaccag gaggtaatct gggcgcacag
aatttatctg agtctgctgc tgtgaaggag atactgaagg agcaggaaaa ccggaaggc
ctgatagccg ccatctgtgc aggtcctact gctctgttgg ctcatgaaat aggctgtgga
agtaaagtta caacacaccc tcttgctaaa gacaaaatga tgaatggagg tcattacacc
tactctgaga atcgtgtgga aaaagacggc ctgattctta caagccgggg gcctgggacc
agcttcgagt ttgcgcttgc aattgttgaa gccctgaatg gcaaggaggt ggcggctcaa
gtgaaggctc cacttgttct taaagactag SEQ ID NO 2
MASKRALVILAKGAEEMETVIPVDVMRRAGIKVTVAGLAGKDPVQCSRDVVICPDASLEDAKKEGPYDVVVLP
GGNLGAQNLSESAAVKEILKEQENRKGLIAAICAGPTALLAHEIGFGSKVTTHPLAKDKMMNGGHYTYSENRV
EKDGLILTSRGPGTSFEFALAIVEALNGKEVAAQVKAPLVLKD

SEQ ID NO 3
ALVILAK

SEQ ID NO 4
DGLILTSR

SEQ ID NO 5
DPVQCSR

SEQ ID NO 6
DVVICPDASLEDAK

SEQ ID NO 7
GAEEMETVIPVDVMR

SEQ ID NO 8
GLIAAICAGPTALLAHEIGFGSK

SEQ ID NO 9
GPGTSFEFALAIVEALNGK

SEQ ID NO 10
GPGTSFEFALAIVEALNGKEVVAQVK

SEQ ID NO 11
KGLIAAICAGPTALLAHEIGFGSK

SEQ ID NO 12
VTTHPLAK

SEQ ID NO 13
VTVAGLAGK

SEQ ID NO 14
VTVAGLAGKDPVQCSR
```

The invention claimed is:

1. A cosmetic method of treating the signs of skin dryness comprising applying an effective amount of at least one polypeptide with an amino acid sequence represented by SEQ ID No. 2, or at least one nucleic acid sequence coding for said polypeptide, to skin in need thereof.

2. The method of claim 1, wherein said polypeptide has an amino acid sequence selected from the group consisting of SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13 and SEQ ID No. 14.

* * * * *